US 11,812,928 B2

(12) United States Patent
Freitag

(10) Patent No.: US 11,812,928 B2
(45) Date of Patent: Nov. 14, 2023

(54) MEDICAL DEVICE

(71) Applicant: Lutz Freitag, Hemer (DE)

(72) Inventor: Lutz Freitag, Hemer (DE)

( * ) Notice: Subject to any disclaimer, the term of this patent is extended or adjusted under 35 U.S.C. 154(b) by 0 days.

(21) Appl. No.: 17/919,441

(22) PCT Filed: Apr. 14, 2021

(86) PCT No.: PCT/EP2021/059673
§ 371 (c)(1),
(2) Date: Oct. 17, 2022

(87) PCT Pub. No.: WO2021/213861
PCT Pub. Date: Oct. 28, 2021

(65) Prior Publication Data
US 2023/0141071 A1     May 11, 2023

(30) Foreign Application Priority Data

Apr. 21, 2020 (DE) ..................... 10 2020 110 840.0

(51) Int. Cl.
*A61B 1/00* (2006.01)
*A61B 1/267* (2006.01)
*A61B 90/00* (2016.01)

(52) U.S. Cl.
CPC ...... *A61B 1/00105* (2013.01); *A61B 1/00066* (2013.01); *A61B 1/00101* (2013.01); *A61B 1/00119* (2013.01); *A61B 1/00128* (2013.01); *A61B 1/2676* (2013.01); *A61B 2090/034* (2016.02)

(58) Field of Classification Search
CPC .......................... A61B 1/00105; A61B 1/00128
See application file for complete search history.

(56) References Cited

U.S. PATENT DOCUMENTS 4,517,962 A * 5/1985 Heckele .................. A61B 1/12
600/172
5,050,585 A   9/1991 Takahashi
5,447,148 A * 9/1995 Oneda ................ A61B 1/00142
600/131

(Continued)

FOREIGN PATENT DOCUMENTS

EP   0 280 384   10/1992
EP   2 097 721   12/2013

OTHER PUBLICATIONS

International Search Report issued by the European Patent Office in International Application PCT/EP2021/059673 dated Jul. 5, 2021.

*Primary Examiner* — Matthew J Kasztejna
(74) *Attorney, Agent, or Firm* — Henry M. Feiereisen LLC

(57) ABSTRACT

A medical device includes an endoscope head which is designed to be detachably connected to endoscope tubes. The endoscope head has a longitudinal channel between a proximal end and a distal end of the endoscope head for receiving an endoscope tube. At least one measuring channel is arranged in the endoscope head. The measuring channel has at least one inner connection opening, which is connected to the longitudinal channel, and at least one outer connection opening, which is arranged on the outside of the endoscope head. The outer connection opening can be connected to at least one measuring channel in a measurement adapter which can be detachably coupled to the endoscope head.

11 Claims, 2 Drawing Sheets

(56) References Cited

U.S. PATENT DOCUMENTS

| | | | |
|---|---|---|---|
| 5,518,501 A | 5/1996 | Oneda et al. | |
| 6,254,061 B1* | 7/2001 | Levine | A61B 1/00135 251/324 |
| 6,632,402 B2* | 10/2003 | Blazewicz | G01N 21/6408 436/136 |
| 7,297,121 B2* | 11/2007 | Turturro | A61B 10/06 600/563 |
| 7,857,755 B2* | 12/2010 | Kupferschmid | A61B 1/00126 600/125 |
| 8,357,099 B2* | 1/2013 | Gunneson | A61M 16/021 600/532 |
| 2005/0043690 A1* | 2/2005 | Todd | A61M 1/772 604/248 |
| 2009/0143996 A1 | 6/2009 | Karlsson et al. | |
| 2017/0258550 A1 | 9/2017 | Vazales | |
| 2018/0279860 A1 | 10/2018 | Krupica | |
| 2021/0212556 A1* | 7/2021 | Nguyen | A61B 1/00066 |

* cited by examiner

MEDICAL DEVICE

CROSS-REFERENCES TO RELATED APPLICATIONS

This application is the U.S. National Stage of International Application No. PCT/EP2021/059673, filed Apr. 14, 2021, which designated the United States and has been published as International Publication No. WO 2021/213861 A1 and which claims the priority of German Patent Application, Serial No. 10 2020 110 840.0, filed Apr. 21, 2020, pursuant to 35 U.S.C. 119(a)-(d).

BACKGROUND OF THE INVENTION

The invention relates to a medical device.

Endoscopes are used for minimally invasive surgical procedures on humans and animals as well as cavities which are difficult to access in the art for visual inspection. Depending on the intended use, endoscope tubes with different diameters find application. In bronchoscopy, rigid bronchoscope tubes of stainless steel with wall thicknesses of 0.6 mm are oftentimes used. Diameters in the range of 10 mm with lengths of approximately 400 mm are customary. For placing the frequently used silicone stents, tube diameters of 10-16 mm are required according to the width of a normal larynx. Handling with thicker equipments for stent insertion requires practice and experience.

A further problem is that in endoscopy, it is normally not possible to change from a smaller diameter to a larger diameter, or vice versa, without greater effort. For this purpose, it normally requires to completely exchange the endoscope tube including the endoscope head attached thereto and to reattach all the connections arranged therein. In the case of bronchoscopy, the connections involve in particular connections for ventilation of the lung and also connections for measuring the pressure conditions within the endoscope.

The invention is based on the object to provide a medical device with an endoscope head which enables the use of different endoscope tubes in a simple manner and to implement the necessary connections with the endoscope head as uncomplicated as possible.

SUMMARY OF THE INVENTION

This object is achieved by a medical device as set forth hereinafter.

The dependent claims relate to advantageous refinements of the invention.

The medical device includes an endoscope head which is designed to be detachably connected to endoscope tubes. For this purpose, the endoscope head has a longitudinal channel between its proximal end and its distal end. In addition, at least one measuring channel is arranged in the endoscope head. The at least one measuring channel has at least one inner connection opening, which is connected to the longitudinal channel, and at least one outer connection opening, which is arranged on the outside of the endoscope head. The outer connection opening can in particular be arranged laterally. Preferably, the measuring channel in the endoscope head is as short as possible. It therefore preferably runs radially. Preferably, two diametrically arranged, radially extending measuring channels are provided in the endoscope head.

The outer connection opening of the at least one measuring channel is connectable to a measurement adapter. The measurement adapter can be detachably coupled to the endoscope head. The measurement adapter serves as link and in particular as quick-action coupling between a measuring instrument, which, for example, is connected via a hose to the measurement adapter and to the endoscope head. The connection of the individual measuring channels is in particular gas-conducting. The invention has the advantage that, even in the case of several measuring channels in the endoscope head, these can be connected to the measurement adapter with a single attachment motion. There is no need to connect each measurement channel individually. As a result, it is possible to prepare the endoscope head in a simple and uncomplicated manner for its application.

The measurement adapter should preferably be coupled to the endoscope head in a particularly simple and quick manner and be able to be removed again as easily as well. It can preferably be coupled to the endoscope head via a plug connection. The connection can be realized without tools. The measurement adapter is preferably configured as a U-shaped clamp. In this case, it has two arms which are connected to one another via a spine as a link. Such an U-shaped clamp can be attached laterally onto the endoscope head. The lateral attachment is possible in a particularly simple and rapid manner. A faulty operation or a slipping of the measurement adapter relative to the endoscope head can be precluded through suitable contact surfaces and guide surfaces.

The measurement adapter is preferably held on the endoscope head by using a clamping force. For this purpose, at least one of the two arms can be designed to be resilient. In particular, the entire measurement adapter is made of a resilient material, so that both arms can be designed resilient due to the material properties. As an alternative or in addition, the spring force can be built up through an elastic deformation of the spine. The arms are slightly bent apart during lateral attachment onto the endoscope head. Slanted surfaces are preferably arranged on the endoscope head and/or at the free ends of the arms and slide on each other so that the clamp is bent open. When the clamp assumes the final position, the arms spring back and rest in a clamping and sealing manner on the endoscope head.

It is considered to be advantageous to make the connection not only clamping, i.e. through force-fitting engagement, but in addition or also as an alternative by a form fit. In the case of correspondingly selected tolerances, a form-fitting connection in attachment direction or in opposition to the attachment direction prevents the measurement adapter from slipping and thus a faulty position, a faulty operation or a falsification of measured values. Provision is therefore made for at least one arm and in particular both arms to have latching projections, by which the measurement adapter can be coupled to the endoscope head in a form-fitting manner. A form fit in attachment direction can already be established by having the spine of a U-shaped clamp contact a contact section of the endoscope head. As a result, the attachment depth can be limited. Lateral guides for one or both arms on the arms and/or on the endoscope head ensure the position of the measurement adapter in longitudinal direction of the endoscope head.

The latching projections are located at a distance from the spine. As a result, a predominant embracing of the endoscope head can be ensured in combination with the spring force of the arms. A complete embracing is possible, but not necessarily required. The latching projections are in particular located at the free ends of the arms. When the measurement adapter is attached, the arms are bent slightly apart with their inwardly directed latching projections. The latching projections slide over the outer side of the endoscope head and ultimately snap behind a latching edge, so that the arms spring back, and so that a sufficiently tight connection is established between the measuring channel or the measuring channels in the endoscope head and the measuring channel or measuring channels in the measurement adapter. In principle, it is also possible to use the spring force of the arms only in such a way as to establish in combination with the latching projections a form-fitting connection in the latching position. It is considered to be particularly beneficial to involve a combination of a form-fitting connection for the positional orientation and force-fitting connection for sealing the transition in the region of the outer connection opening.

As explained above, the measurement adapter is designed to be arranged in a lateral adapter connection region of the endoscope head, with the measurement adapter being displaceable transversely to the longitudinal channel upon the adapter connection region. The latching projections on the free ends of the arms embrace hereby at least two thirds of the endoscope head with respect to its diameter to thereby provide a secure guidance and fixation of the measurement adapter.

Located in the measurement adapter is at least one measuring channel which feeds into the region of the spine of the measurement adapter, in particular in the transition zone to the arms. For this purpose, provision is made in particular for a connection piece in the region of the spine, onto which connection piece in particular a hose can be attached. At least one measuring channel is arranged in one of the arms of the measurement adapter. A measuring channel is preferably arranged in each of the arms of the measurement adapter, which measuring channel can in turn be coupled to a respective outer connection opening of the measuring channel in the endoscope head. Therefore, two connection pieces, which point away from the endoscope head, are preferably located on the spine. Several measuring channels per arm are also possible.

The endoscope head is designed to be detachably connected to endoscope tubes. So that the measuring channel in the endoscope head can also be connected to corresponding measuring channels in the endoscope tube, the endoscope tube has to be aligned in the endoscope head in a particular position. This is reliably possible via a form-fitting connection. In addition, a form-fitting connection between the endoscope tube and the endoscope head has the advantage that a force can be exerted on the endoscope tube via the endoscope head, for example in order to turn it into the correct position. Therefore, the endoscope head is advantageously coupled to the endoscope tube in such a way that the connection is non-rotatable. The fixed rotative engagement can be designed in a force-fitting and/or form-fitting manner. Preferably, the connection is a form fit or primarily a form fit. The form fit can be established by combining a male piece with a matching female piece as a counterpart. For this purpose, at least one male piece on the endoscope tube and/or endoscope head can engage with at least one female piece on the endoscope tube and/or on the endoscope head. In the simplest case, it involves one or more tongue-and-groove connections.

Such a form-fitting connection can simultaneously determine the attachment depth of the endoscope tube into the endoscope head, so that lateral termination openings of the measuring channels on the endoscope tube correspond with the respective connection openings in the endoscope head.

Provision is made in a further refinement of the invention for the endoscope-tube-side male piece or female piece to be formed on an adapter sleeve which can be coupled to a proximal end of the endoscope tube. The adapter sleeve has the necessary form-fitting elements for a rotationally fixed connection with the endoscope head. The adapter sleeve limits the attachment depth of the endoscope tube into the endoscope head and defines the position of the measurement channels. The adapter sleeve also has one or more measuring channels, which can be connected to the measuring channels in the endoscope tubes and can be connected to the measuring channel there through engagement into the longitudinal channel of the endoscope head.

Provision is made in a further refinement of the invention for adapter sleeves with diameters that are matched to one another, so that an adapter sleeve with smaller diameter can be mated with an adapter sleeve of greater diameter. The adapter sleeves have force-fitting connections and/or form-fitting connections to one another and to the components with which they come into engagement. Such adapter sleeves ensure that a force can be transmitted from the endoscope head to a connected endoscope tube via the adapter sleeves and in particular via at least two adapter sleeves. In particular, it is possible to connect an endoscope tube of smaller diameter, which is coupled to the smaller adapter sleeve, to the endoscope head via the adapter sleeve serving as an intermediary sleeve. In this way, it is possible to use endoscope tubes of different thickness with one and the same endoscope head, wherein the thickness compensation is realized via the use of suitable adapter sleeves.

As an alternative to adapter sleeves which are mated with one another with different diameters, but are each matched to the diameter of the endoscope tube, it is also possible within the scope of the invention to use different adapter sleeves which have a first diameter region for coupling to the longitudinal channel of the endoscope tube and a second, optionally smaller diameter region, for connection to the endoscope tube of differing diameter.

In accordance with the configuration of the endoscope tube or endoscope head, the measuring channels are arranged in the adapter sleeves, i.e. in particular diametrically. The length of the measuring channels is as short as possible. The arrangement of the measuring channels is therefore preferably not only diametrically but also radially.

The used endoscope involves in particular a bronchoscope.

BRIEF DESCRIPTION OF THE DRAWING

The invention is explained hereinafter with reference to an exemplary embodiment illustrated in schematic drawings. It is shown in:

FIG. 1 another exploded perspective view of the medical device of FIG. 1.

DETAILED DESCRIPTION OF PREFERRED EMBODIMENTS

Figure 1:
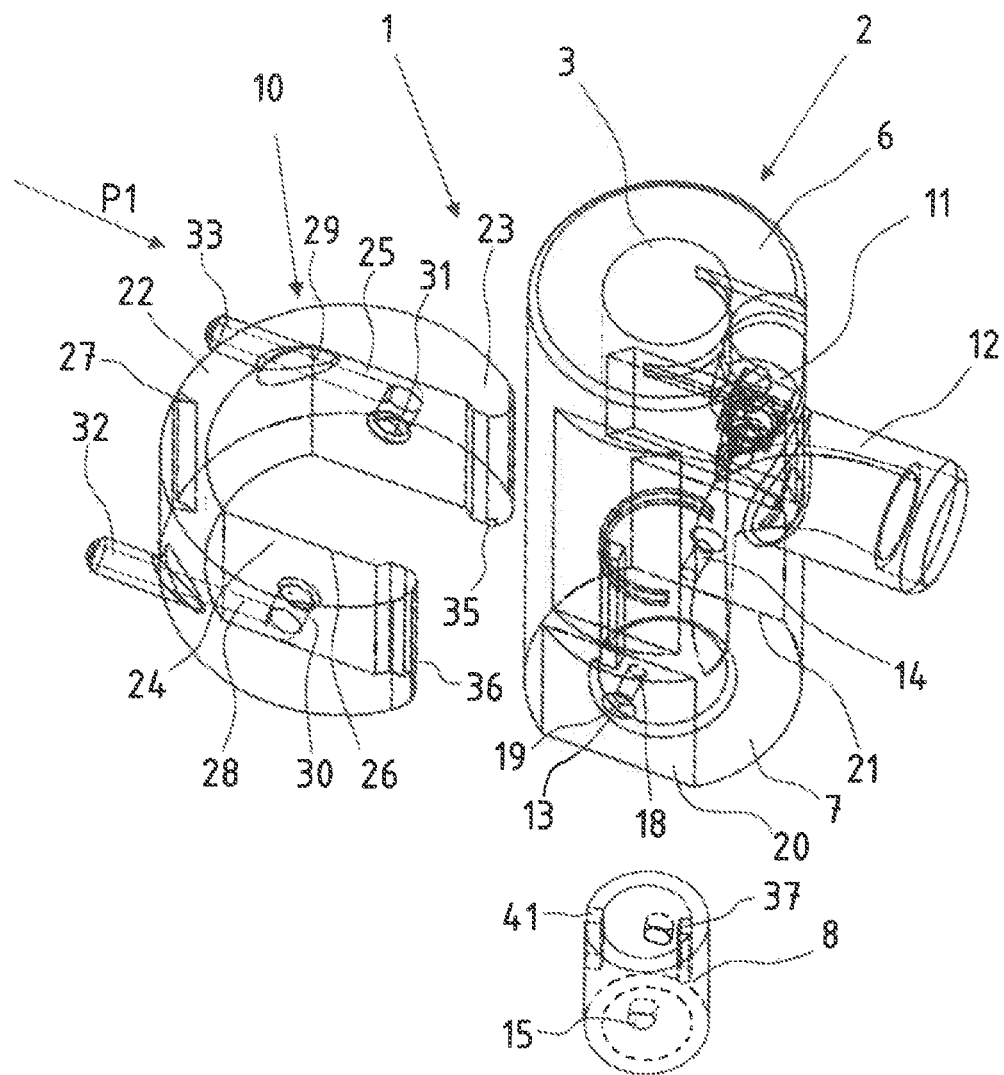
FIG. 1 an exploded perspective view of a medical device according to the invention.
Figure 2:
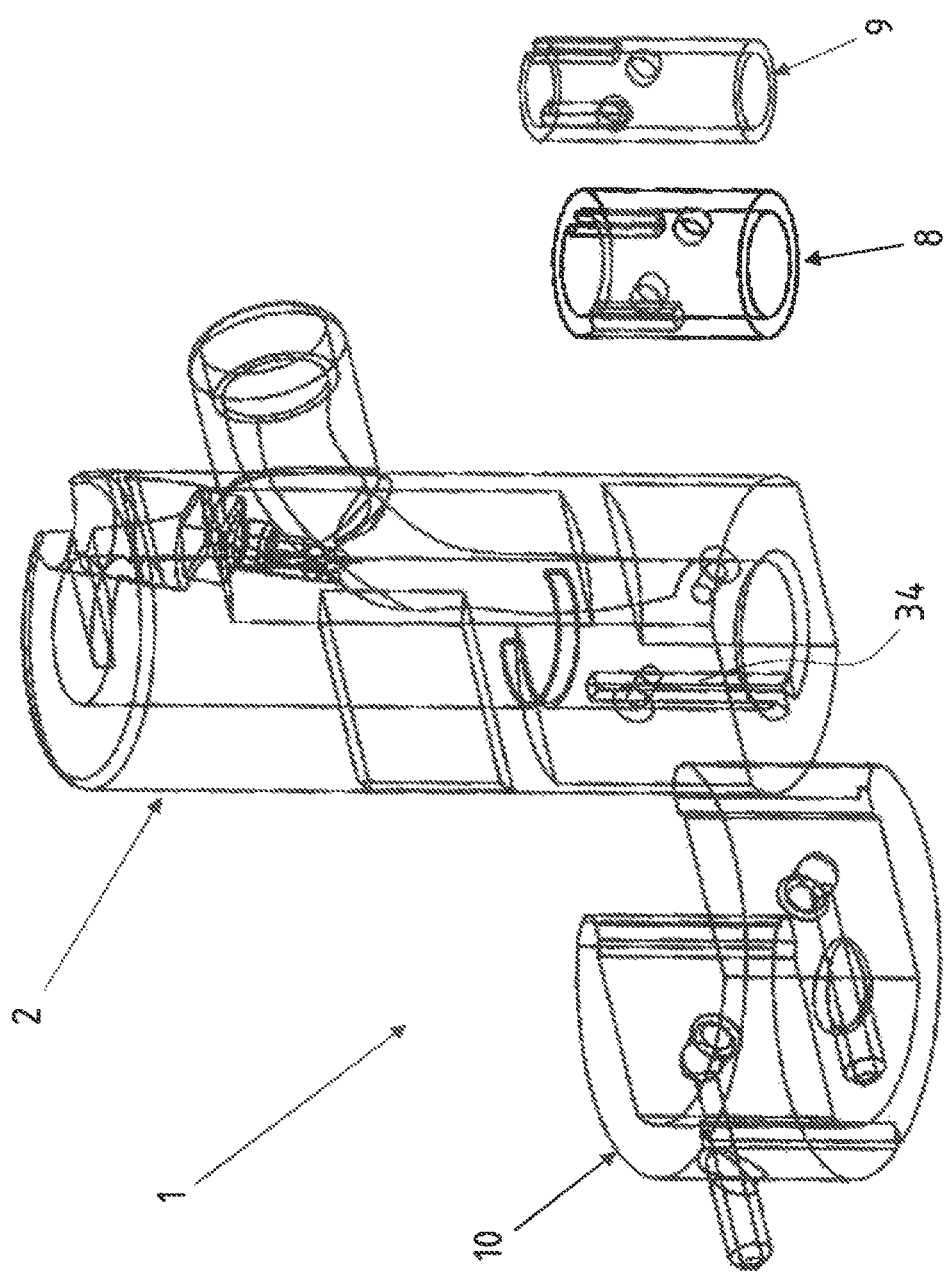

FIGS. 1 and 2 show two different perspective illustrations of one and the same medical device 1 with an endoscope head 2 as a central component. The endoscope head 2 has a longitudinal channel 3 extending vertically in the image plane for receiving an endoscope tube 4. The endoscope tube 4 is only partially shown. FIG. 1 shows only the proximal end 5 thereof. The longitudinal channel 3, which extends from a proximal end 6 to a distal end 7 of the endoscope head 2, serves to receive the proximal end 5 of the endoscope tube 4. The diameter of the endoscope tube 4 is significantly smaller than the inner diameter of the longitudinal channel 3. In order to compensate the diameters, adapter sleeves 8, 9 are used, which will be discussed further below.

A further component of the device 1 is a measurement adapter 10. The measurement adapter 10 can be detachably coupled to the endoscope head 2 by being attached laterally in the direction of the arrow P1 onto the substantially cylindrical endoscope head 2. It can be withdrawn again in the opposite direction. No tool is required for insertion and removal.

In addition to the actual longitudinal channel 3, which serves as a working channel, the endoscope head has connections for ventilation. These connections are provided when the endoscope head is used during bronchoscopy. A first connection 11 serves for jet ventilation. A second connection 12 is provided for common ventilation at lower pressures. The connections 11, 12 can alternatively be used.

In addition, the endoscope head includes measuring channels 13, 14. The measuring channels 13, 14 are arranged diametrically. They are located in the vicinity of the distal end 7, so that they can be brought into overlap with measuring channels 15, 16 in the adapter sleeves 8, 9 or can be connected to a measuring channel 17 in the endoscope tube 4. The measuring channels 13, 14 feed into the longitudinal channel 3 and have each an inner connection opening 18 and an outer connection opening 19. The outer connection opening 19 is located in a lateral adapter connection region 20. Unlike the remaining outer contour of the substantially cylindrical endoscope head 2, the adapter connection region 20 is not rounded, but flattened. Since corresponding connection openings 19 are diametrically opposite each other on the outside, the corresponding adapter connection regions 20, 21 are also arranged opposite one another. The adapter connection regions 20 are flattened and in this case extend parallel to one another. Via these flattened adapter connection regions 20, the measurement adapter 10 can be pushed in direction of the arrow P1. For this purpose, the measurement adapter is configured as an U-shaped clamp. It has a spine 22 and two arms 23, 24 which are connected to the spine 22. The arms 23, 24 are configured in a resilient manner and are designed to come into contact with the adapter connection region 20, 21 with their respective contact surfaces 25, 26 formed on the inside of the arms, but at least to establish a fluid-conducting, in particular gas-conducting connection to the outer connection openings 19 of the measuring channels 13, 14 in the endoscope head 2. The arms 23, 24 have a mutual spacing which is conformed to the distance of the adapter connection regions 20.

For the spring action of the arms 23, 24, a notch 27 is arranged on the outside in the spine 22. As a result, although the arms 23, 24 are able to spring outwards, the spring action is established due to a deformation in the region of the spine 22. The arms 23, 24 themselves do not have to be elastic, but can be.

The measuring channels 13, 14 from the endoscope head 2 are continued by further measuring channels 28, 29 in the measurement adapter 10. Extending in longitudinal direction of the arms 23, 24 are measuring channels 28, 29, respectively. The two measuring channels 28, 29 have each connection openings 30, 31 in the mutually facing contact surfaces 25, 26. The measuring channels 28, 29 are therefore angled within the arms 23, 24. These connection openings 30, 31 correspond in the mated position of the measurement adapter 10 with the connection openings 19 on the endoscope head 2. The measuring channels 28, 29 in the measurement adapter 10 feed each into connecting pieces 32, 33, to each of which a hose can be connected in order to tap and evaluate the pressure at the measurement adapter 10.

Sealing means, not shown in greater detail, are able to seal the measurement adapter 10 in the endoscope head 2 in the transition zone between the measuring channels 28, 29 of the measurement adapter to the measuring channels 13, 14. Sealing may also be realized via a sufficiently large gap seal, for example by resting the contact surfaces 25, 26 in a clamping manner on the adapter connection regions 20, 21. For additional locking, inwardly directed latching projections 35, 36 are provided at the free ends of the arms. These involve bead-like thickenings which, in the mated position, engage behind the flattened lateral adapter connection regions 20 on the endoscope head 2 and thereby prevent an unintentional removal of the measurement adapter 10.

The spine 22 is bent and conformed to the outer contour of the endoscope head 2. It serves as a stop and limits the insertion depth of the measurement adapter 10.

It is an essential prerequisite for a pressure measurement that the measuring channels in the respective components freely extend continuously. For this purpose, it is necessary to align the measuring opening 17 in the endoscope tube 4 in such a way as to be continuously connected to the measuring channel 13, 14 in the endoscope head 2. The exact positioning is ensured by the use of the adapter sleeves 8, 9. In this exemplary embodiment, adapter sleeves 8, 9 of different sizes are used by way of example. The greater of the two adapter sleeves 8 has an outer diameter which is conformed to the inner diameter of the longitudinal channel 3, i.e. can be inserted therein. In addition to the measuring channel 15 arranged there, this adapter sleeve 8 additionally has an inwardly directed radial projection which serves as a male piece 37 for a female piece 38 on the smaller adapter sleeve 9. The female piece 38 is designed as a radially outer, groove-shaped depression. The female piece 38 does not extend over the entire axial length of the adapter sleeve 9, so that the attachment depth into the greater adapter sleeve 8 can be limited and also defined by the length of the female piece 38. The smaller adapter sleeve 9 also has a radially inwardly directed male piece 39 in the form of a radially inwardly pointing longitudinal web. This male piece 39 is intended to engage in a corresponding female piece 40 in the form of a longitudinal notch beginning at the proximal end 5 of the endoscope tube 4. Here, too, the exact position of the endoscope tube 4 in the smaller adapter sleeve 9 is determined by the length of the male piece 39 or female piece 40. The endoscope tube 4 can now be inserted together with the smaller adapter sleeve 9 and with incorporation of the greater adapter sleeve 8 into the endoscope head 2. For alignment and for securing against rotation, the greater adapter sleeve 8 has a female piece 41 in the form of a longitudinal groove extending in the longitudinal direction from its proximal end. This longitudinal groove or this female piece 41 corresponds with a respective web in the form of a male piece 34 (FIG. 2) in the interior of the longitudinal channel 3. In this way, a fixed rotative engagement of the components relative to one another is ensured. In a manner not shown in greater detail, the arrangement of adapter sleeves 8, 9 and endoscope tube 4 can additionally be secured against displacement in the longitudinal direction of the endoscope tube 4. This can involve a clamping connection which acts on the attached endoscope tube 4 radially from the outside and thereby establishes the connection to the endoscope head 2.

The medical device 1 of FIG. 1 enables the use of greater endoscope tubes 4 as well. By dispensing with the smaller adapter sleeve 9, a greater endoscope tube can also be connected directly to the greater one of the adapter sleeves 8 in the same way as shown in FIG. 1.

The invention claimed is:

1. A medical device, comprising:
   an endoscope head designed to be detachably connected to an endoscope tube, said endoscope head including a longitudinal channel extending between a proximal end and a distal end of the endoscope head for receiving the endoscope tube, and a transverse gas-conducting head measuring channel which includes an inner connection opening connected to the longitudinal channel, and an outer connection opening arranged on an outside of the endoscope head; and
   a measurement adapter detachably coupleable to the endoscope head and configured as a U-shaped clamp which includes a spine and two arms resiliently connected to the spine and including a lateral gas-conducting adapter measuring channel connectable to the outer connection opening of the head measuring channel, said arms having free ends at a distance to the spine and formed with latching projections which are directed inwardly towards the endoscope head and which, when the arms are bent apart as the measurement adapter is mated with the endoscope head, slide upon an outer lateral adapter connection region of the endoscope head and snap behind a latching edge of the endoscope head, so that the arms spring back and establish a gas-tight seal between the head measuring channel and the adapter measuring channel.

2. The medical device of claim 1, wherein the spine has an outer side formed with a notch to resiliently connect the two arms to the spine and effect a spring action of the arms.

3. The medical device of claim 1, wherein the arms have each a contact surface resting on the adapter connection region in a clamping manner and providing the seal in form of a gap seal.

4. The medical device of claim 1, wherein the latching projections are bead-like thickenings.

5. The medical device of claim 1, wherein the spine has a bent configuration which is conformed to an outer contour of the endoscope head so as to form a stop for limiting an attachment depth of the measurement adapter into the endoscope head.

6. The medical device of claim 1, wherein the measuring channel in the measurement adapter feeds into the region of the spine.

7. The medical device of claim 1, wherein the endoscope head is coupleable with the endoscope tube in fixed rotative engagement, with the fixed rotative engagement being designed in a force-fitting manner or form-fitting manner by enabling a male piece on the endoscope tube to engage a female piece endoscope head or by enabling a male piece on the endoscope head to engage a female piece on the endoscope tube.

8. The medical device of claim 6, further comprising an adapter sleeve coupleable to a proximal end of the endoscope tube and comprising a male piece constructed to engage the female piece on the endoscope head or a female piece constructed to engage the male piece on the endoscope head.

9. The medical device of claim 8, further comprising a plurality of said adapter sleeve constructed with diameters selected so that a first adapter sleeve with a first inside diameter an a first outside diameter is able to be inserted in a second adapter sleeve with an inside diameter corresponding to the first outside diameter and a second outside diameter greater than the first outside diameter, so that an endoscope tube having an outside diameter corresponding to the first inside diameter and is coupleable with the endoscope head via the first and second adapter sleeve.

10. The medical device of claim 9, wherein the adapter sleeves include measuring channels which are connectable to measuring channels in the endoscope tubes and connectable to the head measuring channel when engaging into the longitudinal channel of the endoscope head.

11. The medical device of claim 1, wherein the endoscope head includes two of said head measuring channel arranged diametrically in the endoscope head.

* * * * *